United States Patent [19]
Ogata et al.

[11] Patent Number: 5,753,658
[45] Date of Patent: May 19, 1998

[54] QUINOLONECARBOXYLIC ACID DERIVATIVES

[75] Inventors: Kazumi Ogata, Toyonaka; Yuuichi Isowaki, Settsu; Hidetoshi Nakao, Itami; Shuuichi Nishihata, Suita, all of Japan

[73] Assignee: Senju Pharmaceutical Co., Ltd., Osaka, Japan

[21] Appl. No.: 193,589

[22] Filed: Feb. 8, 1994

[30] Foreign Application Priority Data

Feb. 9, 1993 [JP] Japan ................... 5-021201
Mar. 1, 1993 [JP] Japan ................... 5-039998

[51] Int. Cl.$^6$ ............... A61K 31/495; A61K 31/47; C07D 401/10
[52] U.S. Cl. ............... 514/254; 514/312; 544/363; 546/156
[58] Field of Search ............... 546/156; 544/363; 514/312, 254

[56] References Cited

U.S. PATENT DOCUMENTS

| 4,556,658 | 12/1985 | Grohe et al. | 514/254 |
| 5,155,223 | 10/1992 | Preiss | 544/363 |
| 5,290,934 | 3/1994 | Ueda et al. | 546/13 |
| 5,395,936 | 3/1995 | Manzo et al. | 544/363 |

FOREIGN PATENT DOCUMENTS

| 121727 | 2/1984 | European Pat. Off. |
| 167763 | 5/1985 | European Pat. Off. |
| 3306771 | 8/1984 | Germany | 544/363 |
| 2094305 | 9/1982 | United Kingdom | 544/363 |
| 94/04505 | 8/1993 | WIPO |

OTHER PUBLICATIONS

Cecchetti et al, *J. Med. Chem.* 36 p. 3449 (1993).
Lopez et al, *Chemical Abstracts*, vol. 113, No. 40731 1990 (Abstract for ES 2006098, Apr. 1, 1989).
Allemandi et al, Journal of *Antimicrobial Chemotherapy* 34 (2) pp. 261–265 (1994).

*Primary Examiner*—Emily Bernhardt
*Attorney, Agent, or Firm*—Millen, White, Zelano, & Branigan, P.C.

[57] ABSTRACT

Presented is a novel quinolonecarboxylic acid derivative of the formula I and its pharmaceutically acceptable salt:

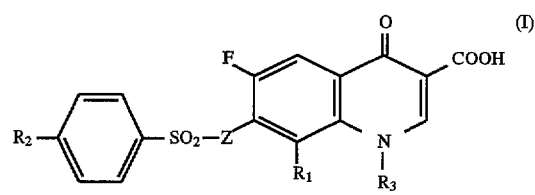

wherein $R_1$ is hydrogen, halogen or lower alkoxy, $R_2$ is hydrogen, lower alkyl, lower alkoxy, —$NH_2$, —$NHCOCH_3$ or halogen, $R_3$ is lower alkyl, and z is a group represented by the formula II or III:

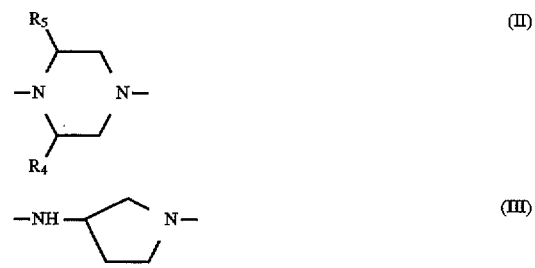

wherein $R_4$ and $R_5$ are identical or different and are hydrogen or lower alkyl. A method of preparation of these compound and a method of treatment of diseases caused by bacterial infection are also presented.

12 Claims, 2 Drawing Sheets

QUINOLONECARBOXYLIC ACID DERIVATIVES

BACKGROUND OF THE INVENTION

The present invention relates to novel quinolonecarboxylic acid derivative and to method of preparation and use thereof.

Since the development of norfloxacin, a wide variety of new quinolone synthetic antibacterials have been newly synthesized and developed. They include, for example, ofloxacin, ciprofloxacin, lomefloxacin, fleroxacin, tosufloxacin, etc.

Upon this background, the inventors searched for a novel quinolonecarboxylic acid derivative having a potent antibacterial activity. They found that such activity exists in a class of novel quinolonecarboxylic acid derivatives which were obtained by a reaction between (i) a quinolonecarboxylic acid derivative having a piperazinyl or pyrrolidinyl group at position 7 of the quinolone ring and (ii) a position 4-substituted benzenesulfonyl halide. The present invention was made on the basis of this finding.

SUMMARY OF THE INVENTION

The invention, therefore, provides compounds of the formula I:

$$R_2 \text{—} \bigcirc \text{—} SO_2 \text{—} Z \text{—} \text{[quinolone core with F, COOH, } R_1, R_3 \text{]} \quad (I)$$

wherein $R_1$ is hydrogen, halogen or lower alkoxy, $R_2$ is hydrogen, lower alkyl, lower alkoxy, —$NH_2$, —$NHCOCH_3$ or halogen, $R_3$ is lower alkyl, and Z is a group represented by the formula II or III:

$$\text{[piperazinyl group with } R_4, R_5 \text{]} \quad (II)$$

$$\text{[pyrrolidinyl group]} \quad (III)$$

wherein $R_4$ and $R_5$, identical or different, are hydrogen or lower alkyl, or a pharmaceutically acceptable salt thereof.

The compounds of the formula I exhibit antibacterial activity against both gram positive and gram negative bacteria.

The invention also provides a method of preparation of such a derivative or salt and, additionally, antibacterial pharmaceutical compositions containing such a derivative or salt, (which derivatives and salts are hereinafter referred to as "the present compounds").

In another method aspect, the invention relates to the use of the compound for the manufacture of a pharmaceutical composition for treatment of diseases caused by bacterial infection of mammals, including humans.

The invention still further provides a method of treatment of diseases caused by bacterial infection of mammals including human comprising orally, parenterally or locally administering to said mammals a pharmacologically effective amount of the present compound.

DETAILED DISCUSSION

Figure 1:
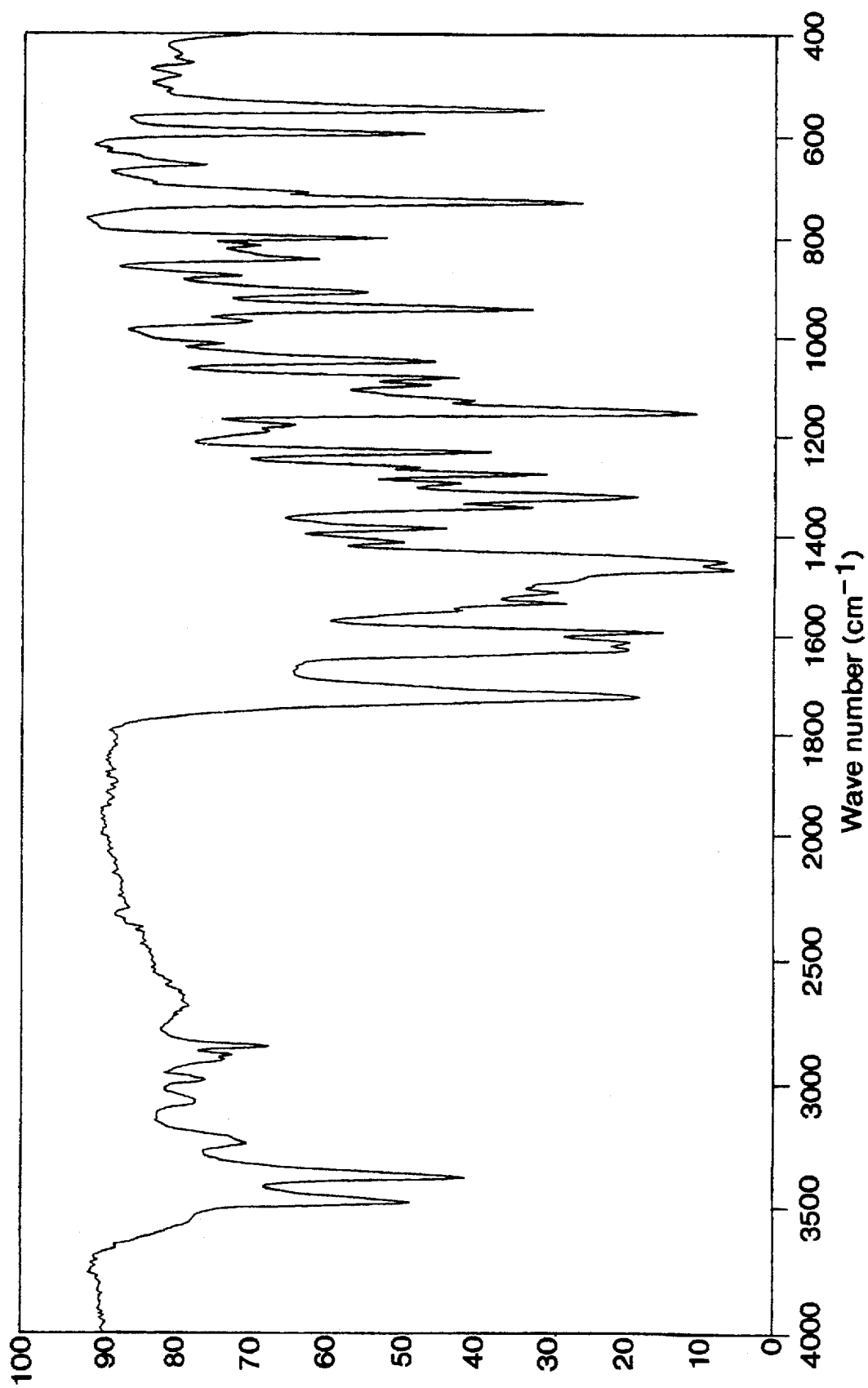
FIG. 1 shows the IR spectrum of the compound obtained in Example 2.

In the present application, the term "halogen" for R, and $R_2$ in formula I, IV or V means chlorine, fluorine, bromine or iodine.

Preferable "lower alkyl" for $R_2$, $R_3$, $R_4$ and $R_5$ in formulas I to V is an alkyl group made up of 1 to 5 carbon atoms, either of straight or branched chain or cyclic. Examples of such lower alkyl include methyl, ethyl, n-propyl, isopropyl, cyclopropyl, n-butyl, isobutyl, tert-butyl, sec-butyl, n-pentyl, 1-ethylpropyl, isopentyl, etc.

Preferable "lower alkoxy" for $R_1$ and $R_2$ in the formula I, IV or V is an alkoxy group made up of 1 to 5 carbon atoms. Examples of such lower alkoxy include methoxy, ethoxy, propoxy, isopropoxy, n-butoxy, isobutoxy, tert-butoxy, n-pentyloxy, neopentyloxy, 2-methylbutoxy, 1,2-dimethylpropoxy, 1-ethylpropoxy, etc.

For the purpose of the present invention, the compound of formula I can be used either in a free form or in the form of a pharmaceutically acceptable salt thereof. Examples of such a salt include alkali metal salts such as sodium salt and potassium salt, and organic amine salts such as ethanolamine salt. However, other salts can also be used if pharmaceutically acceptable.

The compound of formula I can be synthesized as follows:

A compound of formula IV:

$$\text{[quinolone structure with F, COOH, H—Z, } R_1, R_3 \text{]} \quad (IV)$$

wherein $R_1$, $R_3$ and Z are as defined hereinbefore, is allowed to react, in the presence of a base, with a position 4-substituted benzenesulfonyl halide of the formula V:

$$R_2 \text{—} \bigcirc \text{—} SO_2X \quad (V)$$

wherein $R_2$ is as defined hereinbefore, and X is halogen, to give the compound of the formula I. The desired reaction product can then be recovered from the reaction mixture.

The compound of formula IV can be obtained according to, for example, Japanese laid-open patent application No. 47658/1980, Japanese patent publication No. 56151/1987, Japanese laid-open patent applications Nos. 74667/1983, 10574/1986 and 33453/1980, the content of which publications is herein incorporated by reference.

The base aforementioned, which is used as a deacidification agent, preferably is an organic amine such as pyridine or triethylamine. Such a base can be used either alone or as a mixture with a nonpolar solvent such as benzene or tetrahydrofuran (THF). Any solvent can be used provided it does not hinder the above reaction. Preferable temperature for the reaction is approximately 0° C. to room temperature.

The reaction will be completed in approximately 3 to 5 hours. Then, after evaporating off any excess base or solvent, the residue is dissolved in a solution of alkali metal hydroxide, e.g. sodium hydroxide. The solution is then neutralized with an acid, e.g. hydrochloric acid, whereupon crystals of the desired product. A compound in which $R_2$ is —$NH_2$ in formula I can be obtained by hydrolysis of a compound in which $R_2$ is $NHCOCH_3$. For example, the former compound can be obtained in the form of crystals by refluxing the resulting solution of the latter compound in 2N hydrochloric acid at boiling temperature for approximately 1 to 2 hours, and neutralizing the solution with an alkaline compound such as sodium hydroxide.

The purification of the compound obtained as above may be carried out, depending upon the nature of the compound, by precipitation method or by recrystallization from a suitable solvent, e.g. dimethylformamide (DMF)-ethanol. When needed, the compound obtained above may be converted into a salt form by a conventional method, for example by; dissolving the compound in a solution of an alkali metal hydroxide, e.g. sodium or potassium hydroxide, concentrating the solution, and then precipitating the corresponding salt by addition of an alcohol.

The present compound thus obtained is unknown in the prior art (not described in any prior publications). It is useful as an antibacterial against both gram positive and gram negative bacteria, and, therefore it can be used (i.e., for example, orally, parenterally or locally administered) to treat diseases caused by bacterial infection, either gram positive or gram negative, of mammals including human.

The pharmaceutical composition of the present invention, according to purpose and need in individual cases, may contain one or more of the present compounds.

The pharmaceutical composition of the present invention can be a oral, parenteral or topical antibacterial composition. The composition may be prepared in any form by conventional methods, including a solid form such as tablets, granules, powder and capsules, and a liquid form such as injectable solution and eye drops. In preparing such compositions, any conventional additives can be incorporated, such as excipients, binders, thickeners, suspension aids, dispersing agents, reabsorption promoters, buffering agents, surfactants, dissolution aids, preservatives, emulsifiers, isotonizers, stabilizers and pH adjusting agents.

The preferable dose of administration of the compounds of this invention as an antibacterial is, for example, approximately 1 to about 100 mg×once/adult/day for injectable solution and approximately 10 to about 1000 mg×several times/adult/day for oral preparation, although the dose varies depending upon the particular compound used, the body weight or age of the patient, and the type or severity of the disease. In the case of eye drops, it is preferable to administer several times/adult/day those containing about 0.05 to 0.5 w/v % of the present compound.

It is possible that the present pharmaceutical composition may contain other antibacterial components or components with a different type of pharmacological activity.

The following examples are presented as further disclosure and illustration of the present invention and are not intended as a limitation thereof.

EXAMPLE 1

1-Ethyl-6,8-difluoro-1,4-dihydro-4-oxo-7-[4-(4-acetamidobenzenesulfonyl)-1-piperazinyl]-3-quinolinecarboxylic acid ($R_1$=F, $R_2$=—$NHCOCH_3$, $R_3$=ethyl, $R_4$=H, $R_5$=H, Z=piperazinyl)

2.80 g of 1-ethyl-6,8-difluoro-1,4-dihydro-4-oxo-7-(1-piperazinyl)-3-quinolinecarboxylic acid is suspended in 100 ml of pyridine. To this suspension is slowly added 7.76 g of 4-acetamidobenzenesulfonyl chloride in 20 ml of benzene under ice-cooling while stirring. Stirring is continued for 1 hour under ice-cooling and then for further 3 hours at room temperature. The reaction mixture is concentrated under reduced pressure. To the residue is added 1N sodium hydroxide solution to dissolve. The pH of the solution is then adjusted to 4 with acetic acid. Precipitating crystals are collected by filtration, washed with water and recrystallized from dimethylformamide (DMF)-ethanol to give 4.10 g of the titled compound. Melting point: 276°–277° C.

Elementary analysis: for $C_{24}H_{24}N_4F_2O_6S$ . 3/4 $H_2O$ Calculated (%): C, 52.60 ; H, 4.69 ; N, 10.22 Found (%): C, 52.70 ; H, 4.75 ; N, 10.17

EXAMPLE 2

1-Ethyl-6,8-difluoro-1,4-dihydro-4-oxo-7-[4-(4-aminobenzenesulfonyl)-1-piperazinyl]-3-quinolinecarboxylic acid ($R_1$=F, $R_2$=—$NH_2$, $R_3$=ethyl, $R_4$=H, $R_5$=H, Z=piperazinyl)

A mixture of 2.15 g of 1-ethyl-6,8-difluoro-1,4-dihydro-4-oxo-7-[4-(4-acetamidobenzenesulfonyl)-1-piperazinyl]-3-quinolinecarboxylic acid obtained in Example 1, 100 ml of 2N hydrochloric acid and 50 ml of ethanol is refluxed for 2 hours while stirring. The reaction mixture is then concentrated under reduced pressure. To the residue is added 1N sodium hydroxide solution to dissolve. The pH of the solution is adjusted to 7.0 with acetic acid.

Precipitating crystals are collected by filtration and then washed with water. To the crystals filtered off is added water, and the pH is adjusted to 4 with acetic acid to dissolve. After filtering off of any undissolved matter, the filtrate is adjusted to pH 7.0 with 2N sodium hydroxide solution. Precipitated crystals are collected by filtration and washed with water. The crystals are then recrystallized from dimethylformamide (DMF)-ethanol to give 1.63 g of the titled compound. Melting point: 274°–275° C. The IR spectrum is shown in FIG. 1.

Elementary analysis: for $C_{22}H_{22}N_4F2O_5S$ Calculated (%): C, 53.65 ; H, 4.50 ; N, 11.38 Found (%): C, 53.43 ; H, 4.62 ; N, 11.14

EXAMPLE 3

1-Ethyl-6,8-difluoro-1,4-dihydro-4-oxo-7-(4-benzenesulfonyl-1-piperazinyl)-3-quinolinecarboxylic acid ($R_2$=F, $R_2$=H, $R_3$=ethyl, $R_4$=H, $R_5$=H, Z=piperazinyl)

1.19 g of the titled compound is obtained analogously to Example 1 by using as starting materials 1.00 g of 1-ethyl-6,8-difluoro-1,4-dihydro-4-oxo-7-(1-piperazinyl)-3-quinolinecarboxylic acid and 2.10 g of benzenesulfonyl chloride. Melting point: 234°–235° C.

Elementary analysis: for $C_{22}H_{21}N_3F_2O_5S$ Calculated (%): C, 55.34 ; H, 4.43 ; N, 8.80 Found (%): C, 55.47 ; H, 4.47 ; N, 8.77

EXAMPLE 4

1-Ethyl-6,8-difluoro-1,4-dihydro-4-oxo-7-[4-(4-methylbenzenesulfonyl)-1-piperazinyl]-3-quinolinecarboxylic acid ($R_1$=F, $R_2$=methyl, $R_3$=ethyl, $R_4$=H, $R_5$=H, Z=piperazinyl)

2.45 g of the titled compound is obtained analogously to Example 1 by using as starting materials 1.90 g of 1-ethyl- 6,8-difluoro-1,4-dihydro-4-oxo-7-(1-piperazinyl)-3-quinolinecarboxylic acid and 4.27 g of 4-toluenesulfonyl chloride. Melting point: 236°–237° C.

Elementary analysis: for $C_{23}H_{23}N_3F_2O_5S$ Calculated (%): C, 56.20 ; H, 4.72 ; N, 8.55 Found (%): C, 56.45 ; H, 4.81 ; N, 8.72

EXAMPLE 5

1-Ethyl-6,8-difluoro-1,4-dihydro-4-oxo-7-[4-(4-methoxybenzenesulfonyl)-1-piperazinyl]-3-quinolinecarboxylic acid ($R_1$=F, $R_2$=methoxy, $R_3$=ethyl, $R_4$=H, $R_5$=H, Z=piperazinyl)

1.21 g of the titled compound is obtained analogously to Example 1 by using as starting materials 0.88 g of 1-ethyl-6,8-difluoro-1,4-dihydro-4-oxo-7-(1-piperazinyl)-3-quinolinecarboxylic acid and 2.16 g of 4-methoxybenzenesulfonyl chloride. Melting point: 252°–253° C.

Elementary analysis: for $C_{23}H_{23}N_3F_2O_6S$ Calculated (%): C, 54.43 ; H, 4.57 ; N, 8.28 Found (%): C, 54.39 ; H, 4.53 ; N, 8.28

EXAMPLE 6

1-Ethyl-6,8-difluoro-1,4-dihydro-4-oxo-7-[4-(4-chlorobenzenesulfonyl)-1-piperazinyl]-3-quinolinecarboxylic acid ($R_1$=F, $R_2$=Cl, $R_3$=ethyl, $R_4$=H, $R_5$=H, Z=piperazinyl)

1.06 g of the titled compound (as pale pink crystals) is obtained analogously to Example 1 by using as starting materials 1.01 g of 1-ethyl-6,8-difluoro-1,4-dihydro-4-oxo-7-(1-piperazinyl)-3-quinolinecarboxylic acid and 2.53 g of 4-chlorobenzenesulfonyl chloride. Melting point: 231°–233° C.

Elementary analysis: for $C_{22}H_{20}N_3ClF_2O_5S$ Calculated (%): C, 51.62 ; H, 3.94 ; N, 8.21 Found (%): C, 51.64 ; H, 3.99 ; N, 8.04

EXAMPLE 7

1-Ethyl-6,8-difluoro-1,4-dihydro-4-oxo-7-[4-(4-fluorobenzenesulfonyl)-1-piperazinyl]-3-quinolinecarboxylic acid ($R_1$=F, $R_2$=F, $R_3$=ethyl, $R_4$=H, $R_5$=H, Z=piperazinyl)

1.07 g of the titled compound (as pale pink crystals) is obtained analogously to Example 1 by using as starting materials 1.01 g of 1-ethyl-6,8-difluoro-1,4-dihydro-4-oxo-7-(1-piperazinyl)-3-quinolinecarboxylic acid and 2.38 g of 4-fluorobenzenesulfonyl chloride. Melting point: 243°–244° C.

Figure 2:
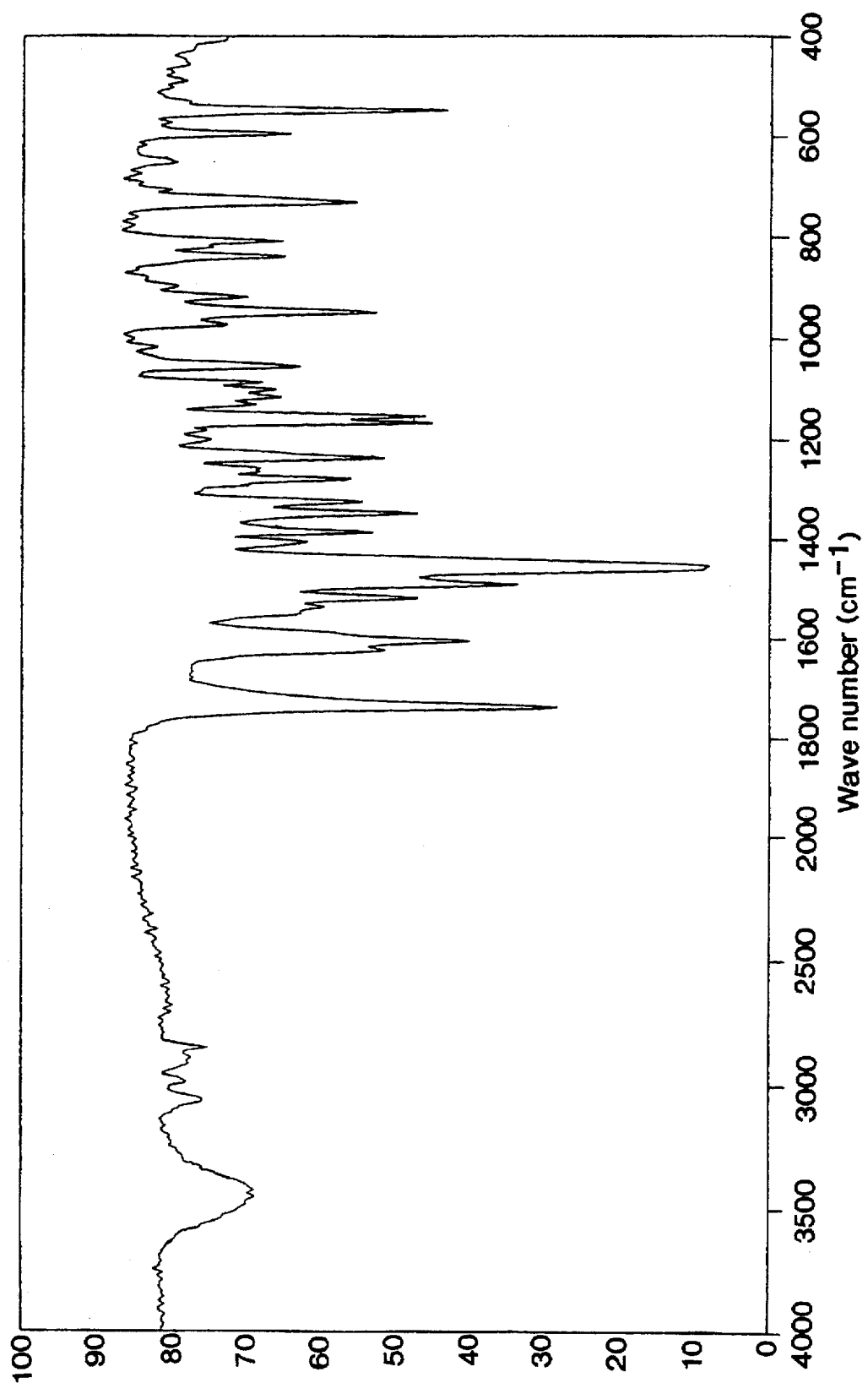
FIG. 2 shows the IR spectrum of the compound obtained in Example 7.

The IR spectrum is shown in FIG. 2.

Elementary analysis: for $C_{22}H_{20}N_3F_3O_5S$ Calculated (%): C, 53.33 ; H, 4.07 ; N, 8.48 Found (%): C, 53.24 ; H, 4.05 ; N, 8.34

EXAMPLE 8

1-Ethyl-6-fluoro-1,4-dihydro-4-oxo-7-[4-(4-aminobenzenesulfonyl)-1-piperazinyl]-3-quinolinecarboxylic acid ($R_1$=H, $R_2$=—$NH_2$, $R_3$=ethyl, $R_4$=H, $R_5$=H, Z=piperazinyl)

0.85 g of the titled compound is obtained analogously to Examples 1 and 2 by using as starting materials 1.73 g of 1-ethyl-6-fluoro-1,4-dihydro-4-oxo-7-(1-piperazinyl)-3-quinolinecarboxylic acid and 5.08 g of 4-acetamidobenzenesulfonyl chloride. Melting point: 283°–284 ° C.

Elementary analysis: for $C_{22}H_{23}N_4FO_5S$ . 1/4 $H_2O$ Calculated (%): C, 55.11 ; H, 4.94 ; N, 11.68 Found (%): C, 55.07 ; H, 5.11 ; N, 11.61

EXAMPLE 9

1-Cyclopropyl-6,8-difluoro-1,4-dihydro-4-oxo-7-[4-(4-acetamidobenzenesulfonyl)-1-piperazinyl]-3-quinoline-carboxylic acid ($R_1$=F, $R_2$=—$NHCOCH_3$, $R_3$=cyclopropyl, $R_4$=H, $R_5$=H, Z=piperazinyl)

2.17 g of the titled compound is obtained analogously to Example 1 by using as starting materials 1.85 g of 1-cyclopropyl-6,8-difluoro-1,4-dihydro-4-oxo-7-(1-piperazinyl)-3-quinolinecarboxylic acid and 4.95 g of 4-acetamidobenzenesulfonyl chloride. Melting point: 282°–284° C.

Elementary analysis: for $C_{25}H_{24}N_4F_2O_6S$ . 1/4 $H_2O$ Calculated (%): C, 54.49 ; H, 4.48 ; N, 10.17 Found (%): C, 54.54 ; H, 4.48 ; N, 10.09

EXAMPLE 10

1-Cyclopropyl-6,8-difluoro-1,4-dihydro-4-oxo-7-[4-(4-aminobenzenesulfonyl)-1-piperazinyl]-3-quinolinecarboxylic acid ($R_1$=F, $R_2$=—$NH_2$, $R_3$=cyclopropyl, $R_4$=H, $R_5$=H, Z=piperazinyl)

2.15 g of the titled compound is obtained analogously to Example 2 by using as a starting material 2.15 g of 1-cyclopropyl-6,8-difluoro-1,4-dihydro-4-oxo-7-[4-(4-acetamidobenzenesulfonyl)-1-piperazinyl]-3-quinolinecarboxylic acid obtained in Example 9. Melting point: 280–282° C.

Elementary analysis: for $C_{23}H_{22}N_4F_2O_5S$ . 1/4 $H_2O$ Calculated (%): C, 54.27 ; H, 4.46 ; N, 11.01 Found (%): C, 54.29 ; H, 4.46 ; N, 11.02

EXAMPLE 11

1-Isobutyl-6,8-difluoro-1,4-dihydro-4-oxo-7-[4-(4-acetamidobenzenesulfonyl)-1-piperazinyl]-3-quinoline-carboxylic acid ($R_1$=F, $R_2$=—$NHCOCH_3$, $R_3$=isobutyl, $R_4$=H, $R_5$=H, Z=piperazinyl)

4.53 g of the titled compound is obtained analogously to Example 1 by using as starting materials 3.10 g of 1-isobutyl-6,8-difluoro-1,4-dihydro-4-oxo-7-(1-piperazinyl)-3-quinolinecarboxylic acid and 3.97 g of 4-acetamidobenzenesulfonyl chloride. Melting point: 181°–183 ° C.

Elementary analysis: for $C_{26}H_{28}N_4F_2O_6S$ . $H_2O$ Calculated (%): C, 53.79 ; H, 5.21 ; N, 9.65 Found (%): C, 53.98 ; H, 5.21 ; N, 9.78

EXAMPLE 12

1-Isobutyl-6,8-difluoro-1,4-dihydro-4-oxo-7-[4-(4-aminobenzenesulfonyl)-1-piperazinyl]-3-quinolinecarboxylic acid ($R_1$=F, $R_2$=—$NH_2$, $R_3$=isobutyl, $R_4$=H, $R_5$=H, Z=piperazinyl)

A mixture of 4.16 g of 1-isobutyl-6,8-difluoro-1,4-dihydro-4-oxo-7-[4-(4-acetamidobenzenesulfonyl)-1-piperazinyl]-3-quinolinecarboxylic acid obtained in Example 11, 150 ml of 6N hydrochloric acid and 20 ml of ethanol is refluxed for 2 hours while stirring. The reaction mixture is then concentrated under reduced pressure. To the residue is added 2N sodium hydroxide solution to dissolve. The pH of the solution is adjusted to 7.0 with acetic acid.

Precipitated crystals are collected by filtration and washed with water to give 3.57 g of the titled compound. Melting point: 256°–258° C.

Elementary analysis: for $C_{24}H_{26}N_4F_2O_5S \cdot 1/4 H_2O$ Calculated (%): C, 54.90 ; H, 5.09 ; N, 10.67 Found (%): C, 54.92 ; H, 5.05 ; N, 10.83

EXAMPLE 13

1-Ethyl-6-fluoro-1,4-dihydro-4-oxo-7-[4-(4-aminobenzenesulfonyl)-1-piperazinyl]-8-methoxy-3-quinolinecarboxylic acid ($R_1$=—$OCH_3$, $R_2$=—$NH_2$, $R_3$=ethyl, $R_4$=H, $R_5$=H, Z=piperazinyl)

2.16 g of 1-ethyl-6,8-difluoro-1,4-dihydro-4-oxo-7-[4-(4-acetamidobenzenesulfonyl)-1-piperazinyl]-3-quinolinecarboxylic acid obtained in Example 1 is dissolved in 100 ml of dimethylformamide (DMF). To this is added 7.72 g of 28% sodium methylate and the mixture is refluxed for 2 hours while heating. Then, the reaction mixture is concentrated under reduced pressure. To the residue is added water to dissolve and the solution is neutralized with 2N hydrochloric acid. The precipitated crystals are collected by filtration to give 2.0 g of 1-ethyl-6-fluoro-1,4-dihydro-4-oxo-7-[4-(4-acetamidobenzenesulfonyl)-1-piperazinyl]-8-methoxy-3-quinolinecarboxylic acid. This is suspended in 2N sodium hydroxide solution, and the suspension is refluxed for 2 hours while stirring. The reaction mixture is adjusted to pH 7.0 with acetic acid. The precipitated crystals are collected by filtration and washed with water to give 1.22 g of the titled compound. Melting point: 145° C. (decomp.)

Elementary analysis: for $C_{23}H_{25}N_4F_2O_6S \cdot 2 H_2O$ Calculated (%): C, 51.10 ; H, 5.41 ; N, 10.36 Found (%): C, 51.10 ; H, 5.40 ; N, 10.15

EXAMPLE 14

1-Ethyl-6,8-difluoro-1,4-dihydro-4-oxo-7-[3-(4-acetamidobenzenesulfonamido)-1-pyrrolidinyl]-3-quinolinecarboxylic acid ($R_1$=F, $R_2$=—$NHCOCH_3$, $R_3$=ethyl, Z=pyrrolidinyl)

2.80 g of 1-ethyl-6,8-difluoro-1,4-dihydro-4-oxo-7-(3-amino-1-pyrrolidinyl)-3-quinolinecarboxylic acid (see REFERENCE SYNTHESIS EXAMPLE hereinafter) is suspended in 100 ml of pyridine. To this is slowly added 3.88 g of 4-acetamidobenzenesulfonyl chloride in 20 ml of benzene. The mixture is stirred for 1 hour under ice-cooling and then overnight at room temperature. After evaporating off the solvent from the reaction mixture, the residue is added water and then adjusted to pH 12 with 2N sodium hydroxide solution. Any undissolved matter, if present, is filtered off. The filtrate is adjusted to pH 7 with acetic acid. The precipitated crystals are collected by filtration and washed. The crystals are then suspended in 100 ml of water. The suspension is adjusted to pH 4 with acetic acid, stirred and then filtered to recover the crystals, which are then thoroughly washed with water. The crude crystals thus obtained are dissolved in dimethylformamide (DMF), treated with activated charcoal, and recrystallized from DMF-methanol to give 1.45 g of the titled compound.

REFERENCE SYNTHESIS EXAMPLE

1-Ethyl-6,8-difluoro-1,4-dihydro-4-oxo-7-(3-amino-1-pyrrolidinyl)-3-quinolinecarboxylic acid 3.21 g of 1-ethyl-6,7,8-trifluoro-1,4-dihydro-4-oxo-3-quinolinecarboxylic acid ethyl ester is dissolved in 100 ml of pyridine, and to this solution is added 5.50 g of 3-acetamidopyrrolidine. The mixture is refluxed for 1 hours.

The reaction mixture is then allowed to cool, evaporated under reduced pressure to remove the solvent. The residue is then added water and extracted with chloroform. Following the desiccation of the organic phase, the phase is concentrated under reduced pressure. Crystallization is achieved using diethyl ether. Recrystallization from chloroform-diethyl ether gives 4.0 g of 1-ethyl-6,8-difluoro-1,4-dihydro-4-oxo-7-(3-acetamido-1-pyrrolidinyl)-3-quinolinecarboxylic acid ethyl ester. 4.0 g of this compound is dissolved in 2N sodium hydroxide solution, and the resulting solution is refluxed for 4 hours. The reaction mixture, after cooling, is neutralized with acetic acid. The precipitated crystals are collected by filtration and washed with water. The crystals are then added to 100 ml of water. The mixture is adjusted to pH 4 with acetic acid, and then, after removing any undissolved matter, to pH 7 with 2N sodium hydroxide solution. The precipitated crystals are collected by filtration, washed with water to give 2.8 g of 1-ethyl-6,8-difluoro-1,4-dihydro-4-oxo-7-(3-amino-1-pyrrolidinyl)-3-quinolinecarboxylic acid.

EXAMPLE 15

1-Ethyl-6,8-difluoro-1,4-dihydro-4-oxo-7-[3-(4-aminobenzenesulfonamido)-1-pyrrolidinyl]-3-quinolinecarboxylic acid ($R_1$=F, $R_2$=—$NH_2$, $R_3$=ethyl, Z=pyrrolidinyl)

To the compound obtained in Example 14 is added a mixture solution made up of 100 ml of 2N hydrochloric acid and 10 ml of ethanol, and the resulting mixture is refluxed for 4 hours while heating. After cooling, the reaction mixture is neutralized with 2N sodium hydroxide solution and concentrated under reduced pressure. The residue is added to water which is then adjusted to pH 13 with 2N sodium hydroxide solution to dissolve, and any undissolved matter, if present, is removed. The solution is adjusted to pH 7 with acetic acid. Precipitating crystals are collected by filtration and washed. To the washed crystals is added water, pH adjusted to 3 to dissolve, and any undissolved matter, if present, is removed. The solution is then adjusted to pH 7 with 2N sodium hydroxide solution and precipitating crystals are collected by filtration and washed with water. Recrystallization from DMF-methanol gives 1.07 g of the titled compound. Melting point 214°–216° C.

Elementary analysis: for $C_{22}H_{22}N_4F_2O_6S \cdot H_2O$ Calculated (%): C, 51.76 ; H, 4.74 ; N, 10.97 Found (%): C, 51.92 ; H, 4.60 ; N, 11.00

ANTIBACTERIAL TEST

Antibacterial activity of the compound of the present invention:

The antibacterial activity of the present compounds was evaluated.

Methods

Antibacterial test was carried out according to the method designated by Japan Society of Chemotherapy in *Chemotherapy*, 29 (1): 76 (1981), the content of which is herein incorporated by reference. Each of the compounds obtained in Examples 2, 4 and 7 is tested. As a control drug, 1-ethyl-6,8-difluoro-1,4-dihydro-4-oxo-7-(1-piperazinyl)-3-quinolinecarboxylic acid was used, which is represented by formula IV when $R_1$ is hydrogen, $R_3$ is ethyl, $R_4$ and $R_5$ are hydrogen, and Z is piperazinyl.

The results are shown in Table 1 in terms of minimum inhibitory concentration (MIC).

TABLE 1

| | MIC µg/ml, 10⁶ cells/ml | | | | |
|---|---|---|---|---|---|
| Tested bacterium | Gram's stain | Ex. 2 | Ex. 4 | Ex. 7 | Control drug |
| S. aureus IFO 13276 | + | 0.20 | 0.78 | 0.78 | 0.39 |
| P. aeruginosa IFO 13275 | − | 0.025> | 0.025> | 0.025> | 0.025> |

S. = Staphylococcus, P. = Pseudomonas, Ex. XXX = the compound obtained in Example XXX As Table 1 indicates, the tested compounds of the present invention exhibited a potent antibacterial activity against both the gram negative and gram positive bacteria tested. In particular, the compound obtained in Example 2 exhibited a more potent antibacterial activity than the control drug against S. aureus.

EXAMPLE 16

ORAL TABLETS

| | |
|---|---|
| 1-Ethyl-6,8-difluoro-1,4-dihydro-4-oxo-7-[4-(4-aminobenzenesulfonyl)-1-piperazinyl]-3-quinolinecarboxylic acid (the compound obtained in Example 2) | 100 mg |
| Lactose | 80 mg |
| Starch | 17 mg |
| Magnesium stearate | 3 mg |

Oral tablets can be produced by a conventional method using above components for a single tablet.

What is claimed is:

1. A compound of the following formula:

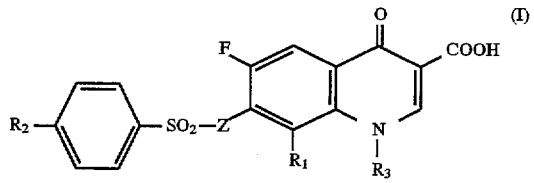

wherein $R_1$ is hydrogen or halogen, $R_2$ is lower alkoxy, —$NH_2$ or —$NHCOCH_3$, $R_3$ is lower alkyl or cycloalkyl, and Z is a group represented by the formula II:

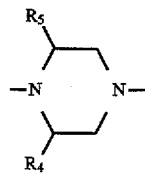

wherein $R_4$ and $R_5$, identical or different, are hydrogen, lower alkyl or cycloalkyl, or a pharmaceutically acceptable salt thereof.

2. A compound of claim 1 which is 1-ethyl-6,8-difluoro-1,4-dihydro-4-oxo-7-[4-(4-acetamidobenzenesulfonyl)-1-piperazinyl]-3-quinolinecarboxylic acid or a pharmaceutically acceptable salt thereof.

3. A compound of claim 1 which is 1-ethyl-6,8-difluoro-1,4-dihydro-4-oxo-7-[4-(4-aminobenzenesulfonyl)-1-piperazinyl]-3-quinolinecarboxylic acid or a pharmaceutically acceptable salt thereof.

4. A compound of claim 1 which is 1-ethyl-6,8-difluoro-1,4-dihydro-4-oxo-7-[4-(4-methoxybenzenesulfonyl)-1-piperazinyl]-3-quinolinecarboxylic acid or a pharmaceutically acceptable salt thereof.

5. A compound of claim 1 which is 1-ethyl-6-fluoro-1,4-dihydro-4-oxo-7-[4-(4-aminobenzenesulfonyl)-1-piperazinyl]-3-quinolinecarboxylic acid or a pharmaceutically acceptable salt thereof.

6. A compound which is 1-ethyl-6,8-difluoro-1,4-dihydro-4-oxo-7-[3-(4-acetamidobenzenesulfonamido)-1-pyrrolidinyl]-3-quinolinecarboxylic acid or a pharmaceutically acceptable salt thereof.

7. A compound of which is 1-ethyl-6,8-difluoro-1,4-dihydro-4-oxo-7-[3-(4-aminobenzenesulfonamido)-1-pyrrolidinyl]-3-quinolinecarboxylic acid or a pharmaceutically acceptable salt thereof.

8. A 7-(4-[4-aminophenyl)sulphonyl]-1-piperazinyl) fluorquinolonic derivative, having the formula:

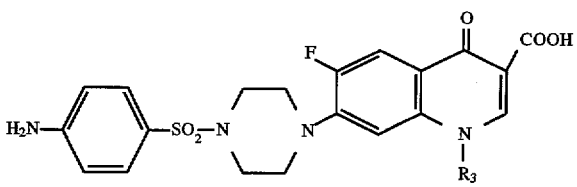

wherein $R_3$ represents $C_1$–$C_5$ alkyl.

9. An antibacterial pharmaceutical composition comprising in admixture with pharmaceutically acceptable carrier a compound of claim 1.

10. A method of treatment of diseases caused bacterial infection of mammals including human comprising orally, parenterally or locally administering to said mammals a pharmacologically effective amount of a compound of claim 1.

11. A method for preparation of a compound of claim 1 or a pharmaceutically acceptable salt thereof comprising:

reacting a compound of the following formula:

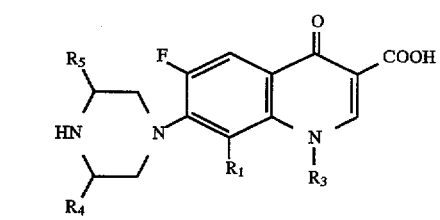

wherein $R_1$, $R_3$, $R_4$ and $R_5$ are as defined, with a compound of the following formula:

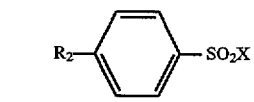

wherein $R_2$ is as defined, and

X is halogen.

12. The method of claim 11, wherein $R_2$ is —$NHCOCH_3$, further comprising hydrolyzing the —$NHCOCH_3$ group to a —$NH_2$ group.

* * * * *